(12) United States Patent
Soper (10) Patent No.: US 12,373,942 B2
(45) Date of Patent: Jul. 29, 2025

(54) SYSTEMS AND METHODS FOR PROGRESSIVE REGISTRATION

(71) Applicant: INTUITIVE SURGICAL OPERATIONS, INC., Sunnyvale, CA (US)

(72) Inventor: Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 534 days.

(21) Appl. No.: 17/786,379

(22) PCT Filed: Dec. 17, 2020

(86) PCT No.: PCT/US2020/065695
§ 371 (c)(1),
(2) Date: Jun. 16, 2022

(87) PCT Pub. No.: WO2021/127237
PCT Pub. Date: Jun. 24, 2021

(65) Prior Publication Data
US 2023/0011019 A1    Jan. 12, 2023

Related U.S. Application Data

(60) Provisional application No. 62/951,835, filed on Dec. 20, 2019.

(51) Int. Cl.
*G06T 7/00*    (2017.01)
*A61B 34/10*   (2016.01)
(Continued)

(52) U.S. Cl.
CPC ............ *G06T 7/0012* (2013.01); *A61B 34/10* (2016.02); *G06T 7/50* (2017.01); *G06V 10/242* (2022.01); *A61B 2034/107* (2016.02)

(58) Field of Classification Search
CPC ............... G06T 7/0012; G06T 7/50; G06T 2207/30061; G06T 7/33; A61B 34/10; A61B 2034/107; G06V 10/242
(Continued)

(56) References Cited

U.S. PATENT DOCUMENTS 6,389,187 B1    5/2002   Greenaway et al.
7,772,541 B2    8/2010   Froggatt et al.
(Continued)

FOREIGN PATENT DOCUMENTS

WO    WO-2017030913 A2    2/2017
WO    WO-2018085287 A1    5/2018

OTHER PUBLICATIONS

International Preliminary Report on Patentability for Application No. PCT/US2020/065695, mailed on Jun. 30, 2022, 9 pages.
(Continued)

*Primary Examiner* — Neil R McLean
(74) *Attorney, Agent, or Firm* — Haynes & Boone, LLP.

(57) ABSTRACT

A system receives a first set of points corresponding to an anatomical feature. Each point in the first set of points represents a position in a first frame. The system receives a second set of points corresponding to the anatomical feature. Each point in the second set of points represents a position in a second frame. The system identifies a first subset of the first set of points and determines a first transformation to align the first subset of the first set of points with the second set of points. The first set of points is transformed based on the first transformation. The system identifies a second subset of the first set of points and determines a second transformation to align the first and second subsets of the first set of points with the second set of points. The first set of points are transformed based on the second transformation.

20 Claims, 7 Drawing Sheets

(51) Int. Cl.
 *G06T 7/50* (2017.01)
 *G06V 10/24* (2022.01)
(58) Field of Classification Search
 USPC .......................................................... 382/128
 See application file for complete search history.

(56) References Cited

U.S. PATENT DOCUMENTS

| | | | |
|---|---|---|---|
| 10,824,896 B2 * | 11/2020 | Xiang | ..................... G06T 7/187 |
| 11,972,582 B2 * | 4/2024 | Yan | ........................... G06T 7/75 |
| 2006/0013523 A1 | 1/2006 | Childlers et al. | |

OTHER PUBLICATIONS

International Search Report and Written Opinion for Application No. PCT/US2020/065695, mailed Apr. 7, 2021, 14 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Ujkani E., et al., "Visual Marker Guided Point Cloud Registration in a Large Multi-sensor Industrial Robot Cell," IEEE/ASME International Conference on Mechtronic and Embedded Systems and Applications, MESA, Jul. 2018, pp. 1-6.

* cited by examiner

SYSTEMS AND METHODS FOR PROGRESSIVE REGISTRATION

CROSS-REFERENCE TO RELATED APPLICATIONS

This application is the U.S. National Stage patent application of International Patent Application No. PCT/US2020/065695 filed on Dec. 17, 2020 which claims the benefit of U.S. Provisional Application 62/951,835 filed Dec. 20, 2019, each of which is incorporated by reference herein in its entirety.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Consistent with some embodiments, a system may receive a first set of points corresponding to an anatomical feature. Each point in the first set of points represents a position in a first frame. The system receives a second set of points corresponding to the anatomical feature. Each point in the second set of points represents a position in a second frame. The system identifies a first subset of the first set of points and determines a first transformation to align the first subset of the first set of points with the second set of points. The first set of points is transformed based on the first transformation. The system identifies a second subset of the first set of points and determines a second transformation to align the first and second subsets of the first set of points with the second set of points. The first set of points are transformed based on the second transformation.

Consistent with some embodiments, a non-transitory machine-readable medium comprises a plurality of machine-readable instructions which when executed by one or more processors associated with a computer-assisted medical system device are adapted to cause the one or more processors to perform a method. The method comprises receiving a first set of points corresponding to an anatomical feature. Each point in the first set of points represents a position in a first reference frame. The method also comprises receiving a second set of points corresponding to the anatomical feature. Each point in the second set of points represents a position in a second reference frame. The method also comprises identifying a first subset of the first set of points and determining a first transformation to align the first subset of the first set of points with the second set of points. The method also comprises transforming the first set of points based on the first transformation and identifying a second subset of the first set of points. The method also comprises determining a second transformation to align the first and second subsets of the first set of points with the second set of points and transforming the first set of points based on the second transformation.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The techniques disclosed in this document may be used to register a medical instrument reference frame to an anatomic image reference frame. A set of location points gathered by a survey instrument in the medical instrument reference frame may be matched to a set of points representing structures such as branched passageways in the anatomic image reference frame. A point matching registration technique, such as an iterative closest point technique (ICP), can be used to register the survey instrument set of points with anatomic image set of points. This registration may rotate, translate, or otherwise manipulate by rigid or non-rigid transforms points associated with image data and points associated surveyed instrument position data so that they are optimally aligned. Though iterative registration approaches such as ICP are commonly guaranteed to converge to a locally optimal solution in a least-squares sense, such solutions may not be globally optimal, or the "true" best solution. The occurrence of these false local minima are common for point-based models of dense and complex branched passageways because the registration algorithms are more likely to converge to false local minima. As described in detail below, a progressive iterative point matching technique has been developed that may anchor registration initially around anatomic areas with fewer, larger, and more rigid passageway's and continues the registration by progressively matching anatomic areas farther from the initial area that may comprise smaller, more densely packed, and more deformable passageways. The techniques for first registering more stable portions of the models and progressively expanding outward toward more complex or variable portions of the models may be used for any forms of registration, including point- or image-based registrations.

Figure 1A:
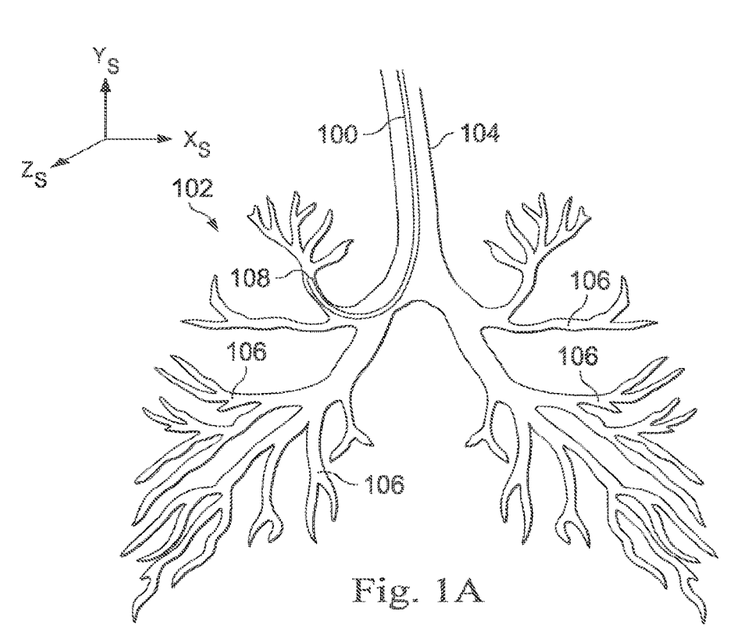
FIG. 1A illustrates a survey instrument extended within a patient anatomy according to some embodiments.
Figure 1B:
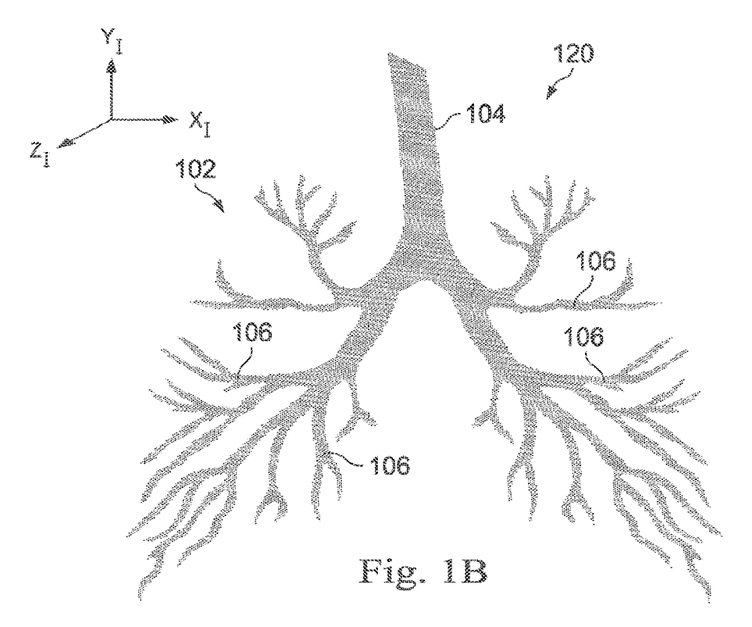
FIG. 1B illustrates an image of the patient anatomy generated by an imaging system.

FIG. 1A. illustrates an elongated survey instrument 100 extending within an anatomic feature such as branched anatomic passageways 102 of an anatomic region such as human lungs. These anatomic passageways 102 include the trachea 104 and the bronchial tubes 106. The survey instrument 100 may be advanced through the trachea 104 and the bronchial tubes 106 to survey the anatomic passageways 102 by gathering location information for the survey instrument 100 in a survey instrument reference frame. The surveyed location information may be recorded as a set of coordinate points, in a coordinate system $X_S$, $Y_S$, $Z_S$, of the survey instrument reference frame. The surveyed points may represent the locations for a distal end 108 of the survey instrument 100 or for regions along the length of the survey instrument 100. The surveyed points may form a survey model for use in registration with different models of the branched anatomic passageways 102, FIG. 1B illustrates an image 120 of the branched anatomic passageways 102, including the trachea 104 and bronchial tubes 106 in an image reference frame coordinate system $X_I$, $Y_I$, $Z_I$. The image 120 may be generated from pre-operative or intra-operative image data obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity-based information) images.

Figure 2:
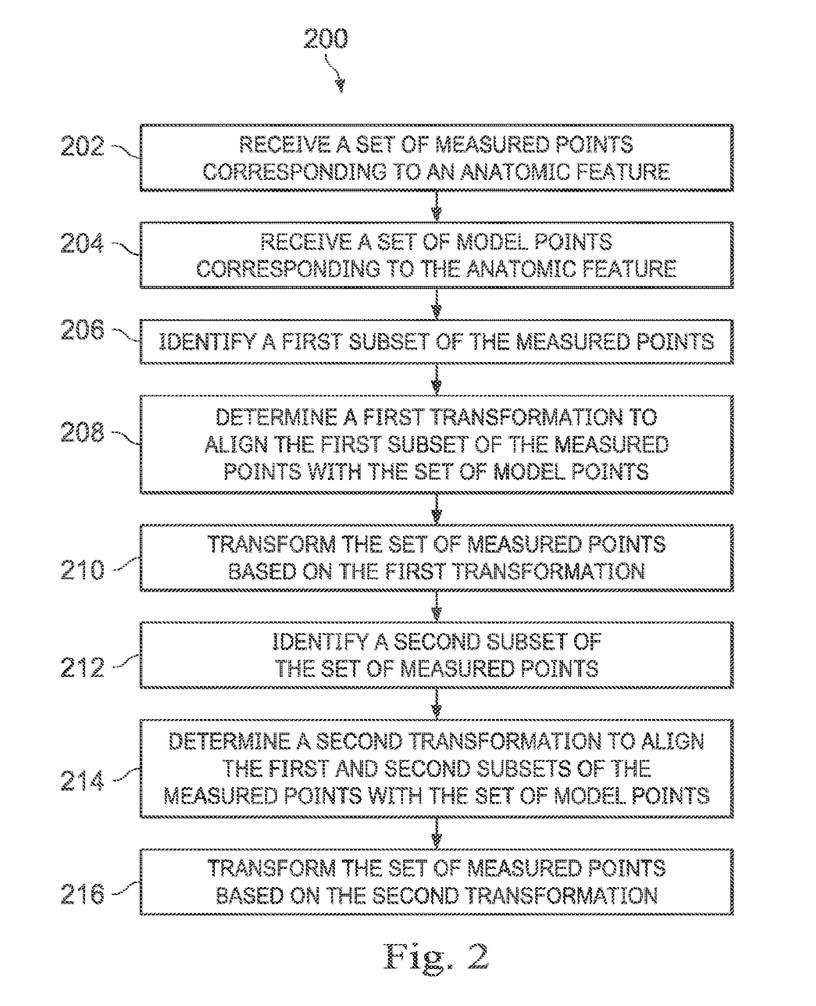
FIG. 2 illustrates a method for determining a registration between models of an anatomic structure according to some embodiments.

FIG. 2 illustrates a method 200 for registering a first set of points of the anatomic structure, such as points collected by a survey instrument 100 within an anatomic feature such as the branched passageways 102, to a second set of points of the anatomic structure, such as those extracted from the image 120 of the anatomy. The method 200 is illustrated as a set of operations or processes 202 through 216 and is described with continuing reference to FIGS. 3-7.

Figure 3:
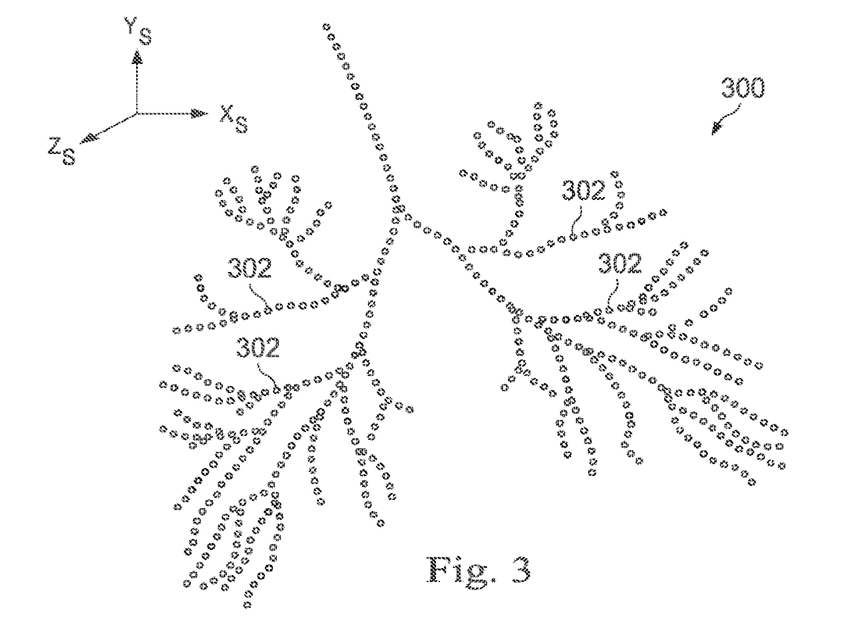
FIG. 3 illustrates a model of an anatomic structure including a plurality of surveyed points collected by a survey instrument according to some embodiments.
Figure 8:
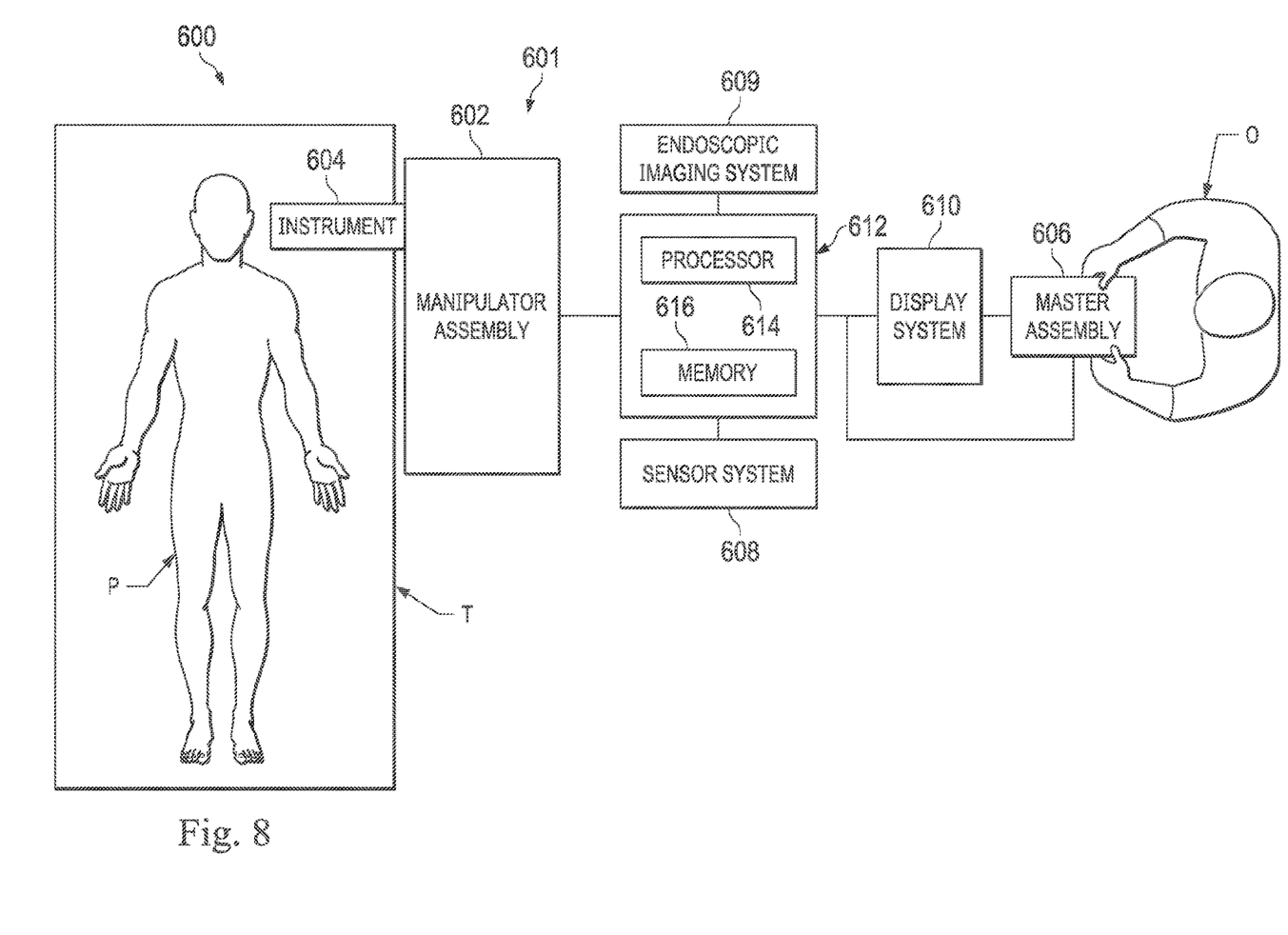
FIG. 8 illustrates a simplified diagram of a robotic or teleoperated medical system according to some embodiments.

At a process 202, a first set of points for a first anatomic coordinate frame is received by, for example, a control system (See FIG. 8, control system 612). As illustrated in FIG. 3, a plurality of points 302 may be the surveyed or measured points in the survey instrument reference frame $X_S$, $Y_S$, $Z_S$ collected by a survey instrument (e.g., survey instrument 100). In some embodiments, the plurality of measured point 302 may be collectively considered a model 300 of an anatomic structure or feature (e.g. the branched anatomic passageways 102). The measured points 302 may be recorded positions of the distal end 108 of the survey instrument 100 during a survey procedure, as the instrument traverses the passageways 102. In alternative embodiments, the measured points 302 may be record positions along the length of the survey instrument 100 as the instrument traverses the passageway's 102.

Figure 4:
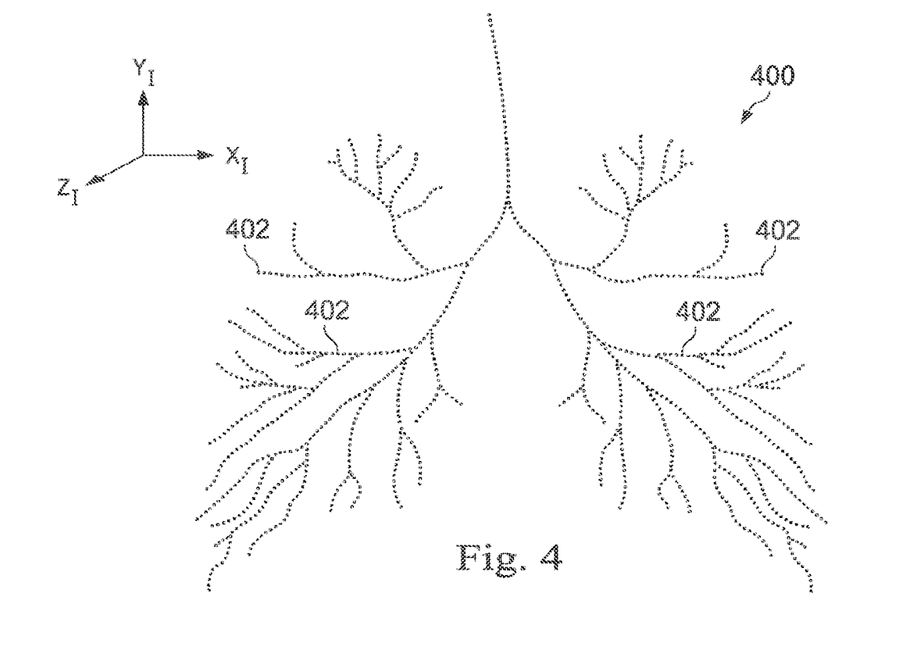
FIG. 4 illustrates a model of an anatomic structure including a plurality of points generated from image data according to some embodiments.

At a process 204, a second set of points for a second anatomic coordinate frame is received by the control system. For example, the second set of points may be model points from an image (e.g., image 120) generated model of the anatomy. As illustrated in Fla 4, a model 400 of the anatomic structure (e.g. the branched anatomic passageways 102) includes a plurality of model points 402 in a coordinate system $X_I$, $Y_I$, $Z_I$, of the image reference frame. The model 400 may be generated, for example, from the image 120, generated from pre-operative or intra-operative image data obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity-based information) images. For example, the image data may be CT image data of the lungs with anatomic passageways 102. Computer software alone or in combination with manual input may be used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. The model may include a centerline model that includes a set of interconnected line segments or points extending through the centers of the modeled passageways. The structures of the model or line segments of the centerline model may be converted to the cloud or set of image model points 402.

Figure 5:
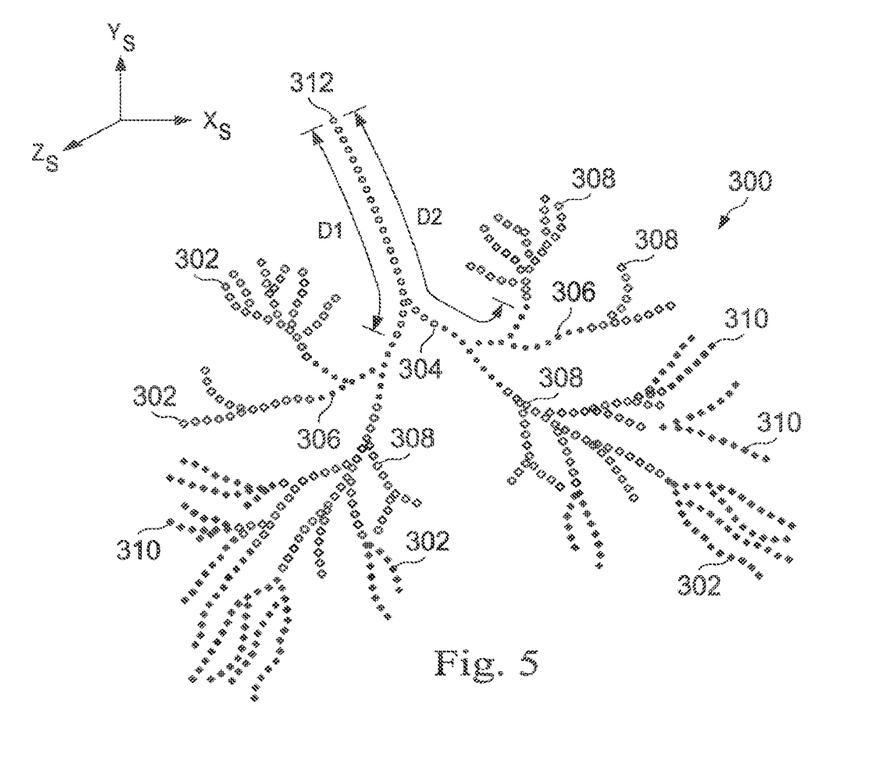
FIG. 5 illustrates the plurality of surveyed points of FIG. 3 grouped into subsets for progressive registration according to some embodiments.

At a process 206, a first subset of points from the first coordinate frame is identified. For example, FIG. 5 illustrates the plurality of measured points 302. (e.g. surveyed points) grouped into subsets 304-310. The subsets 304-310 may be defined based upon a distance or an insertion depth of the survey instrument from a predetermined point 312, The point 312 may be identified by a user or may correspond to a natural location such as the top of the patient trachea or the main carina. In the embodiment of FIG. 5, the subset 304 of the measured points 302 corresponds to an area of the branched anatomy that is relatively uncomplicated with passageways that are few in number, large, and stable. The subset 304 is in a region that extends a distance D1 from the point 312. Additional subsets of the measured points 302 are defined at progressively greater distances from the point 312 which may correspond to progressively greater extension lengths of the survey instrument. For example, the subset 306 of the measured points 302 extends distally from the subset 304 and are at a greater distance range from the predetermined point 312 than the subset 304. The subset 306 is in a region that extends between the distance D1 and a distance D2 from the point 312. In some embodiments the distance D2 is approximately 2 cm greater than the distance D1. In other embodiments the distance D2 may be less than or greater than 2 cm. The subset 306 corresponds to an area of the branched anatomy that is more complicated than the subset 304, with a greater number and smaller passageways. The subset 308 of the measured points 302 extends distally from the subset 306 and are at a greater distance range from the predetermined point 312 than the subset 306. The subset 308 corresponds to an area of the branched anatomy that is more complicated than the subset. 306, with a greater number and smaller passageways. The subset 310 of the measured points 302 extends distally from the subset 308 and are at a greater distance range from the predetermined point 312 than the subset 308. The subset 310 corresponds to an area of the branched anatomy that is more complicated than the subset 308, with a greater number and smaller passageways. In this deepest, most distal region of the anatomy, the passageways may also be less resistant to deformation than the passageways in the higher regions. Each of the regions 306-310 may have a depth of approximately 2 cm but the depth of each region may vary. The first subset chosen in the process 206 may be the subset 304 which has a few, easily identifiable passageways.

Figure 6:
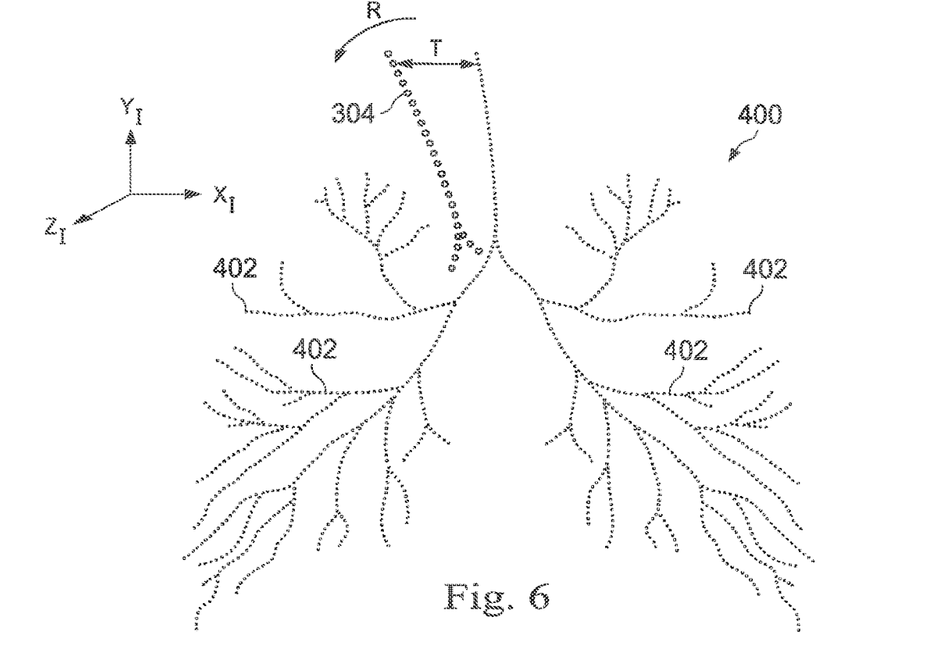
FIG. 6 illustrates one of the subsets of FIG. 5 in transformation to align with the model of the anatomic structure of FIG. 4 according to some embodiments.

Referring again to FIG. 2, at a process 208, a first transformation is determined to align or provide an initial registration of the first subset of points in the first coordinate frame with the second set of model points in the second coordinate frame. For example, as illustrated in FIG. 6, the subset 304 of the measured points 302 is transformed to align with the image model 400. The transformation may be a rigid transformation including three-dimensional rotation components R and three-dimensional translation components T. In some embodiments, the subset 304 includes one or more seed points with a known reference position and orientation in both the image and instrument reference frames. In the lungs, the main carina may be associated with the seed point.

At a process 210, the first set of measured points 302 (e.g. the surveyed points), including the subset 304, may be transformed based on the first transformation determined at process 208.

At a process 212, a second subset of the first set of measured points 302 is identified. The second subset may be the next adjacent subset, after the initial subset, in the distal progression of the measured points 302. For example, with reference to FIG. 5, the second subset may be the subset 306 located distally adjacent to the subset 304, between depths D1 and D2 into the branched anatomy. The second subset 306 may represent an area of the anatomy with more and denser passageways than the first subset 304.

At a process 214, a second transformation is determined to align or provide a registration iteration of the first and second subsets of the first set of model points with the second set of model points. For example, the subsets 304 and 306 of the measured points 302 may be transformed to align with the image model 400. The second transformation may include three-dimensional rotation components and three-dimensional translation components.

At a process 216, the first set of measured points 302 (e.g. the surveyed points), including the subsets 304 and 306, may be transformed based on the second transformation determined at process 214.

The processes 212-216 may be repeated for each of the remaining subsets 308, 310 until a full registration of the surveyed instrument points 302 to the image model points 402 is complete. In some embodiments, the surveyed points 302 may be grouped into a fewer or greater number of subsets. In some embodiments, registrations may be performed with 10 subsets of points. In other embodiments, registrations may be performed with 5 subsets, 20 subsets, or any number of subsets of points.

Figure 7:
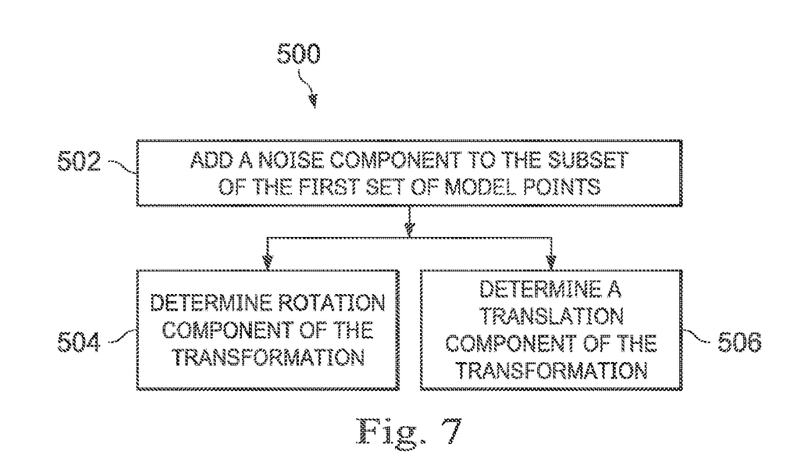
FIG. 7 illustrates a method for determining a transformation according to some embodiments.

In some embodiments, determining the transformation (e.g., processes 208 and/or 214) may include the introduction of noise into the data sets comprising the measured points 302, the model points 402, or both model points 302 and 402. The noise may be generated by perturbing the points 302, 402. In some embodiments, the noise may be random Gaussian noise. In some embodiments the noise changes on each iteration of the registration algorithm and is reduced as the algorithm converges closer to the final solution. Introduction of noise into one or more of the datasets may serve to reduce false minima and reduce the likelihood of convergence to a non-optimal registration. In another embodiment, the degree of noise may vary by subset, with earlier points containing less noise and newer points containing greater noise. FIG. 7 illustrates a method 500 that may be used in the processes 208 and 214 for determining a transformation. At a process 502, a noise component may be added to the first subset of model points. For example, a noise component may be introduced to the subset 304 of points 302. The noise may be generated by perturbing the measured points 302 to effectively create more points for matching in an ICP or other point matching registration technique. In some embodiments, a noise component may also be added to the second set of model points 402.

At a process 504 a three-dimensional rotation component of the transformation may be determined, and at a process 506 a three-dimensional transformation component of the transformation may be determined. In some embodiments, the amount or magnitude of the noise component may be different based on the iteration of the registration. For example, during determination of the first transformation at the process 208, the magnitude of the noise component applied to the subset 304 to determine the first transformation may be greater than the magnitude of the noise component applied to the subsets 304, 306 to determine the second transformation at the process 214. Further, reduced a noise component may be applied to subsets 304, 306, 308 to determine a third transformation iteration. In some embodiments, the magnitude of the noise component applied in the iterative registration process may be reduced for each successive transformation, as more subsets (and therefore more points) arc included in the transformation determination. In other embodiments, the magnitude of the noise component may be the same at each iteration of the transformation determination. In other embodiments, the magnitude of the noise component may be varied, selected by a user, or determined in response to known or sensed factors for each iteration of the transformation determination.

In some embodiments, the registration techniques of this disclosure may be used in an image-guided medical procedure performed with a teleoperated medical system as described in further detail below. As shown in FIG. 8, a tele-operated medical system 600 generally includes a manipulator assembly 602 for operating a medical instrument 604 in performing various procedures on a patient P positioned on a table T in a surgical environment 601. The medical instrument 604 may correspond to the instrument 100. The manipulator assembly 602 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated, A master assembly 606, which may be inside or outside of the surgical environment 601, generally includes one or more control devices for controlling manipulator assembly 602. Manipulator assembly 602 supports medical instrument 604 and may optionally include a plurality of actuators or motors that drive inputs on medical instrument 604 in response to commands from a control system 612. The actuators may optionally include drive systems that when coupled to medical instrument 604 may advance medical instrument 604 into a naturally or surgically created anatomic orifice. Other drive systems may move the distal end of medical instrument 604 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 604 for grasping tissue in the jaws of a biopsy device and/or the like.

Teleoperated medical system 600 also includes a display system 610 for displaying an image or representation of the surgical she and medical instrument 604 generated by a sensor system 608 and/or an endoscopic imaging system 609, Display system 610 and master assembly 606 may be oriented so operator O can control medical instrument 604 and master assembly 606 with the perception of telepresence.

In some embodiments, medical instrument 604 may include components for use in surgery, biopsy, ablation, illumination, irrigation, or suction. Optionally medical instrument 604, together with sensor system 608 may be used to gather (e.g., measure or survey) a set of data points corresponding to locations within anatomic passageways of a patient, such as patient P. In some embodiments, medical instrument 604 may include components of the imaging system 609, which may include an imaging scope assembly or imaging instrument that records a concurrent or real-time image of a surgical site and provides the image to the operator or operator O through the display system 610. The concurrent image may be, for example, a two or three-dimensional image captured by an imaging instrument positioned within the surgical site. In some embodiments, the imaging system components that may be integrally or removably coupled to medical instrument 604. However, in some embodiments, a separate endoscope, attached to a separate manipulator assembly may be used with medical instrument 604 to image the surgical site. The imaging system 609 may be implemented as hardware, firmware, software or a combination thereof which interact with or are otherwise executed by one or more computer processors, which may include the processors of the control system 612.

The sensor system 608 may include a position/location sensor system (e.g., an electromagnetic (EM) sensor system) and/or a shape sensor system for determining the position, orientation, speed, velocity, pose, and/or shape of the medical instrument 604.

Teleoperated medical system 600 may also include control system 612. Control system 612 includes at least one memory 616 and at least one computer processor 614 for effecting control between medical instrument 604, master assembly 606, sensor system 608, endoscopic imaging system 609, and display system 610. Control system 612 also includes programmed instructions (e.g., a non-transitory machine-readable medium storing the instructions) to implement some or all of the methods described in accordance with aspects disclosed herein, including instructions for providing information to display system 610.

Control system 612 may optionally further include a virtual visualization system to provide navigation assistance to operator O when controlling medical instrument 604 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

Figure 9:
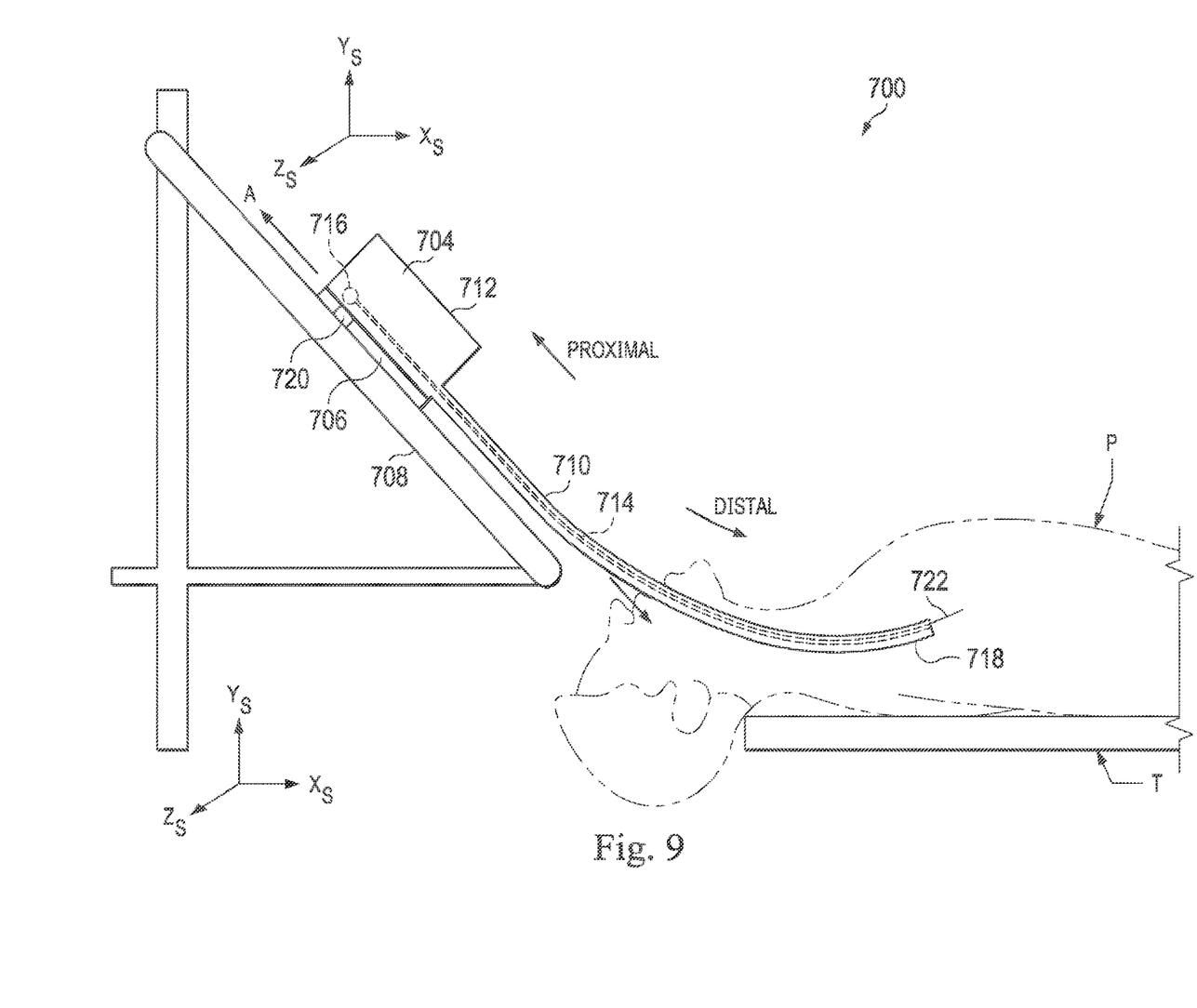
FIG. 9 illustrates a simplified diagram of a medical instrument system according to some embodiments.

FIG. 9 illustrates a surgical environment 700 in which the patient P is positioned on the table T. Patient P may be stationary within the surgical environment in the sense that gross patient movement is limited by sedation, restraint, and/or other means. Cyclic anatomic motion including respiration and cardiac motion of patient P may continue unless tire patient is asked to hold his or her breath to temporarily suspend respiratory motion. Within surgical environment 700, a medical instrument 704 (e.g., the instrument 100, 604), having the instrument frame of reference ($X_S$, $Y_S$, $Z_S$), is coupled to an instrument carriage 706. In this embodiment, medical instrument 704 includes an elongate device 710, such as a flexible catheter, coupled to an instrument body 712, Instrument carriage 706 is mounted to an insertion stage 708 fixed within surgical environment 700. Alternatively, insertion stage 708 may be movable but have a known location (e.g., via a tracking sensor or other tracking device) within surgical environment 700. In these alternatives, the medical instrument frame of reference is fixed or otherwise known relative to the surgical frame of reference. Instrument carriage 706 may be a component of a teleoperational manipulator assembly (e.g., teleoperational manipulator assembly 602) that couples to medical instrument 704 to control insertion motion (i.e., motion along an axis A) and, optionally, motion of a distal end 718 of the elongate device 710 in multiple directions including yaw, pitch, and roll. Instrument carriage 706 or insertion stage 708 may include actuators, such as servomotors, (not shown) that control motion of instrument carriage 706 along insertion stage 708.

In this embodiment, a sensor system (e.g., sensor system 608) includes a shape sensor 714. Shape sensor 714 may include an optical fiber extending within and aligned with elongate device 710. In one embodiment, the optical fiber has a diameter of approximately 200 μm. In other embodiments, the dimensions may be larger or smaller. The optical fiber of shape sensor 714 forms a fiber optic bend sensor for determining the shape of the elongate device 710. In one alternative, optical fibers including Fiber Bragg Gratings (FBGs) arc used to provide strain measurements in structures in one or more dimensions, Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of elongate device 710 can be used to reconstruct the shape of elongate device 710 over the interval of time.

As shown in FIG. 9, instrument body 712 is coupled and fixed relative to instrument carriage 706. In some embodiments, the optical fiber shape sensor 714 is fixed at a proximal point 716 on instrument body 712. In some embodiments, proximal point 716 of optical fiber shape sensor 714 may be movable along with instrument body 712 but the location of proximal point 716 may be known (e.g., via a tracking sensor or other tracking device). Shape sensor 714 measures a shape from proximal point 716 to another point such as distal end 718 of elongate device 710.

Elongate device 710 includes a channel (not shown) sized and shaped to receive a medical instrument 722. In some embodiments, medical instrument 722 may be used for procedures such as surgery, biopsy, ablation, illumination, irrigation, or suction. Medical instrument 722 can be deployed through elongate device 710 and used at a target location within the anatomy. Medical instrument 722 may include, for example, image capture probes, biopsy instruments, laser ablation fibers, and/or other surgical, diagnostic, or therapeutic tools. Medical instrument 722 may be advanced from the distal end 718 of the elongate device 710 to perform the procedure and then retracted back into the channel when the procedure is complete. Medical instrument 722 may be removed from proximal end of elongate device 710 or from another optional instrument port (not shown) along elongate device 710.

Elongate device 710 may also house cables, linkages, or other steeling controls (not shown) to controllably bend distal end 718. In some examples, at least four cables are used to provide independent "up-down" steering to control a pitch of distal end 218 and "left-right" steering to control a yaw of distal end 718.

A position measuring device 720 may provide information about the position of instrument body 712 as it moves on insertion stage 708 along an insertion axis A. Position measuring device 720 array include resolvers, encoders, potentiometers, and/or other sensors that determine the rotation and/or orientation of the actuators controlling the motion of instrument carriage 706 and consequently the motion of instrument body 712. In some embodiments, insertion stage 708 is linear, while in other embodiments, the insertion stage 708 may be curved or have a combination of curved and linear sections.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or inure processors may cause the one or more processors to perform one or more of the processes.

Any alterations and further modifications to the described devices, instruments, methods, and any further application of the principles of the present disclosure are fully, contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROW, a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects old the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a processor; and
    a memory having computer readable instructions stored thereon, the computer readable instructions, when executed by the processor, cause the system to:
        receive a first set of points from one or more sensors of a medical instrument as the medical instrument traverses an anatomical feature, the first set of points corresponding to the anatomical feature, each point in the first set of points representing a position in a first reference frame;
        receive a second set of points from an imaging system, the second set of points corresponding to the anatomical feature, each point in the second set of points representing a position in a second reference frame;
        identify a first subset of the first set of points;
        determine a first transformation to align the first subset of the first set of points with the second set of points;
        transform the first set of points based on the first transformation;
        identify a second subset of the first set of points;
        determine a second transformation to align the first and second subsets of the first set of points with the second set of points; and
        transform the first set of points based on the second transformation.

2. The system of claim 1, wherein the first set of points is generated by an instrument survey of the anatomical feature.

3. The system of claim 1, wherein the second set of points is generated from image data of the anatomical feature.

4. The system of claim 1, wherein the second set of points is disposed along a centerline model of the anatomical feature.

5. The system of claim 1, wherein the second subset of the first set of points is adjacent to the first subset.

6. The system of claim 1, wherein the first subset of the first set of points corresponds to a first region of the anatomical feature, the first region having a first depth from a central bifurcation of the anatomical feature and wherein the second subset of the first set of points correspond to a second region of the anatomical feature, the second region extending from the first depth to a second depth from the central bifurcation.

7. The system of claim 6, wherein the second depth is approximately 2 cm. greater than the first depth.

8. The system of claim 6, wherein the first region of the anatomical feature has a greater rigidity than the second region.

9. The system of claim 6, wherein the first region of the anatomical feature includes fewer branches than the second region.

10. The system of claim 1, wherein the first transformation includes a rotation and translation for the first set of points.

11. The system of claim 1, wherein the computer readable instructions, when executed by the processor, further cause the system to add noise at a first magnitude to the first subset of the first set of points to determine the first transformation.

12. The system of claim 11, wherein the computer readable instructions, when executed by the processor, further cause the system to add noise at a second magnitude to the first and second subsets of the first set of points to determine the second transformation, wherein the first magnitude is greater than the second magnitude.

13. The system of claim 11, wherein the noise is random Gaussian noise.

14. The system of claim 1, wherein the computer readable instructions, when executed by the processor, further cause the system to identify a seed point in the first set of points, the seed point corresponding to a known position and orientation in the second reference frame.

15. The system of claim 14, wherein the known position and orientation is a central bifurcation of the anatomical feature.

16. The system of claim 1, wherein the anatomical feature includes a branched structure.

17. A non-transitory machine-readable medium comprising a plurality of machine-readable instructions which when executed by one or more processors associated with a computer-assisted medical system device are adapted to cause the one or more processors to perform a method comprising:

receiving a first set of points from one or more sensors of a medical instrument as the medical instrument traverses an anatomical feature, the first set of points corresponding to the anatomical feature, each point in the first set of points representing a position in a first reference frame;

receiving a second set of points from an imaging system, the second set of points corresponding to the anatomical feature, each point in the second set of points representing a position in a second reference frame;

identifying a first subset of the first set of points;

determining a first transformation to align the first subset of the first set of points with the second set of points;

transforming the first set of points based on the first transformation;

identifying a second subset of the first set of points;

determining a second transformation to align the first and second subsets of the first set of points with the second set of points; and transforming the first set of points based on the second transformation.

18. The non-transitory machine-readable medium of claim 17, wherein the first set of points is generated by an instrument survey of the anatomical feature.

19. The non-transitory machine-readable medium of claim 17, wherein the second set of points is generated from image data of the anatomical feature.

20. The non-transitory machine-readable medium of claim 17, wherein the first subset of the first set of points corresponds to a first region of the anatomical feature, the first region having a first depth from a central bifurcation of the anatomical feature and wherein the second subset of the first set of points correspond to a second region of the anatomical feature, the second region extending from the first depth to a second depth from the central bifurcation.

* * * * *

UNITED STATES PATENT AND TRADEMARK OFFICE
CERTIFICATE OF CORRECTION

| | | |
|---|---|---|
| PATENT NO. | : 12,373,942 B2 | Page 1 of 1 |
| APPLICATION NO. | : 17/786379 | |
| DATED | : July 29, 2025 | |
| INVENTOR(S) | : Timothy D. Soper | |

It is certified that error appears in the above-identified patent and that said Letters Patent is hereby corrected as shown below:

In the Specification

Column 1, Line 16, change "arc" to -- are --

Column 4, Line 13, change "Fla" to -- FIG --

Column 6, Line 49, change "arc" to -- are --

Column 7, Line 24, change "she" to -- site --

Column 8, Line 22, change "tire" to -- the --

Column 8, Line 54, change "arc" to -- are --

Column 9, Line 33, change "steeling" to -- steering --

Column 9, Line 41, change "array" to -- may --

Column 10, Line 16, change "inure" to -- more --

Column 11, Line 5, change "ROW" to -- ROM --

Column 11, Line 13, change "old" to -- of --

Signed and Sealed this
Sixteenth Day of September, 2025

Coke Morgan Stewart
*Acting Director of the United States Patent and Trademark Office*